US00RE44400E

(19) United States
(12) Reissued Patent
Molin et al.

(10) Patent Number: US RE44,400 E
(45) Date of Reissued Patent: Jul. 30, 2013

(54) **COMPOSITIONS COMPRISING *LACTOBACILLUS PLANTARUM* STRAINS IN COMBINATION WITH TANNIN AND NEW *LACTOBACILLUS PLANTARUM* STRAINS**

(75) Inventors: Göran Molin, Lund (SE); Siv Ahrné, Bjärred (SE); Bengt Jeppsson, Lund (SE)

(73) Assignee: Probi AB (SE)

(21) Appl. No.: 13/070,715

(22) Filed: Mar. 24, 2011

Related U.S. Patent Documents

Reissue of:
(64) Patent No.: 7,507,572
Issued: Mar. 24, 2009
Appl. No.: 10/551,991
PCT Filed: Apr. 2, 2004
PCT No.: PCT/SE2004/000509
§ 371 (c)(1),
(2), (4) Date: Jun. 27, 2006
PCT Pub. No.: WO2004/087893
PCT Pub. Date: Oct. 14, 2004

U.S. Applications:
(60) Provisional application No. 60/463,058, filed on Apr. 16, 2003.

(30) Foreign Application Priority Data

Apr. 4, 2003 (SE) ..... 0300994

(51) Int. Cl.
*C12N 1/20* (2006.01)
*A01N 63/00* (2006.01)

(52) U.S. Cl.
USPC ..... 435/252.9; 435/857; 424/93.45

(58) Field of Classification Search
None
See application file for complete search history.

(56) References Cited

U.S. PATENT DOCUMENTS 5,587,314 A 12/1996 Bengmark et al.
6,159,456 A * 12/2000 Candau ..... 424/59

FOREIGN PATENT DOCUMENTS

| | | |
|---|---|---|
| JP | 01-025726 | 1/1989 |
| JP | 06-166626 | 6/1994 |
| JP | 06-256180 | 9/1994 |
| WO | WO 00/20013 | 4/2000 |
| WO | WO 02/38165 | 5/2002 |

OTHER PUBLICATIONS

A. Hakansson et al, *Rose Hip and Lactobacillus plantarum DSM 9843 Reduce Ischemia/Reperfusion Injury in the Mouse Colon,* 51 Dig. Dis. Sci. 2094-2101 (2006).
K. Niedzielin et al., *A controlled, double-blind, randomized study on the efficacy of Lactobacillus plantarum 299V in patients with irritable bowel syndrome,* 13(10) European Journal of Gastroenteroloy & Hepatology 1143-1147 (2001.
Sören Nobaek et al., "*Alteration Of Intestinal Microflora Is Associated With Reduction In Abdominal Bloating And Pain In Patients With Irritable Bowel Syndrome,*" 95(5) The American Journal of Gastroenterology 1231-1238 (Jul. 2000).
Göran Molin "*Probiotics in foods not containing milk or mil constituents, with special reference to Lactobacillus plantarum 299v*$^{1-3}$," 73(suppl), Am. J. Clin. Nutr. 380S-385S (2001).
Ro Osawa et al., "Isolation of Tannin-Degrading *Lactobacilli* from Humans and Fermented Foods", Applied and Environmental Microbiology, Jul. 2000, pp. 3093-3097, vol. 66, No. 7, American Society for Microbiology (cited in the International Search Report and International Preliminary Report on Patentability.
Lamia Ayed et al., "Culture Conditions of Tannase Production *by Lactobacillus plantarum*", Biotechnology Letters, 2002, pp. 1763-1765, vol. 24 (cited in the International Search Report and International Preliminary Report on Patentability).
Ingegerd Adlerberth et al., "A Mannose-Specific Adherence Mechanism in *Lactobacillus plantarum* Conferring Binding to the Human Colonic Cell Line HT-29", Applied and Environmental Microbiology, Jul. 1996, pp. 2244-2251, vol. 62, No. 7, American Society for Microbiology (cited in the International Search Report).
King-Thom Chung et al., "Tannins and Human Health: A Review", Critical Reviews in Food Science and Nutrition, 1998, pp. 421-464, vol. 38, No. 6, CRC Press LLC (cited in the International Search Report).
M.-L. Johansson et al., "Classification of *Lactobacillus plantarum* by Restriction Endonuclease Analysis of Total Chromosomal DNA Using Conventional Agarose Gel Electrophoresis", International Journal of Systematic Bacteriology, Oct. 1995, pp. 670-675, vol. 45, No. 4, International Union of Microbiological Societies (cited in the International Preliminary Report on Patentability).
M.-L. Johansson et al., "Administration of Different *Lactobacillus* Strains in Fermented Oatmeal Soup: In Vivo Colonization of Human Intestinal Mucosa and Effect on the Indigenous Flora", Jan. 1993, pp. 15-20, vol. 59, No. 1, American Society for Microbiology (cited in the International Preliminary Report on Patentability).

* cited by examiner

*Primary Examiner* — Vera Afremova
(74) *Attorney, Agent, or Firm* — Buchanan Ingersoll & Rooney PC

(57) ABSTRACT

The invention refers to a composition comprising one or more tannase-producing strains of Lactobacillus having the ability to adhere to the human intestinal mucosa in combination with tannin. New tannase-producing strains of Lactobacillus plantarum are a.

14 Claims, 1 Drawing Sheet

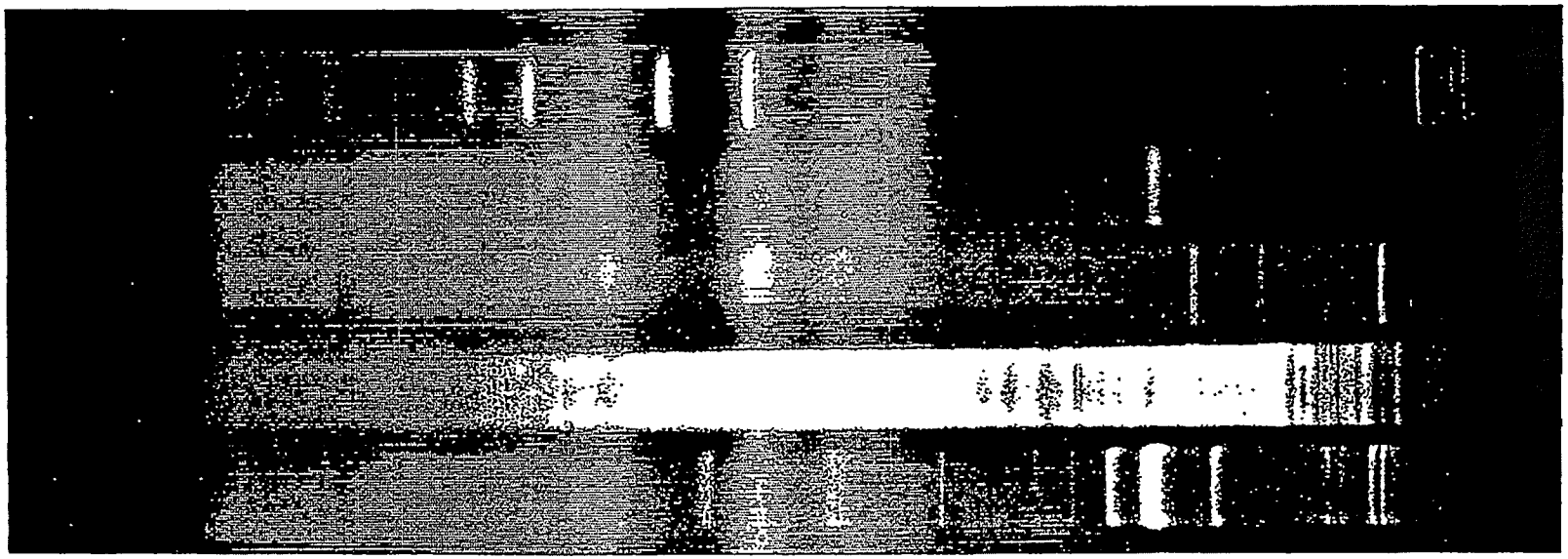
1 2 3 4 5

COMPOSITIONS COMPRISING *LACTOBACILLUS PLANTARUM* STRAINS IN COMBINATION WITH TANNIN AND NEW *LACTOBACILLUS PLANTARUM* STRAINS

Matter enclosed in heavy brackets [ ] appears in the original patent but forms no part of this reissue specification; matter printed in italics indicates the additions made by reissue.

This is *an application for reissue of U.S. Pat. No. 7,507,572, which is* a filing under 35 U.S.C. §371 of International Application No. PCT/SE2004/000509, filed Apr. 2, 2004 that designates the United States of America, and the benefit is claimed under 35 U.S.C. §119(a)-(d) of Swedish Application No. 0300994-1, filed Apr. 4, 2003, and under 35 U.S.C. §119 (e) of U.S. Provisional Application No. 60/463,058, filed Apr. 16, 2003. *More than one reissue has been filed in the reissue of U.S. Pat. No. 7,507,572. The reissue applications are application Ser. No. 13/070,715* (*this application*) *and application Ser. No. 13/910,278.*

The present invention refers to a composition having anti-inflammatory properties and a controlling effect on the intestinal microflora in vivo and preservative properties in vitro, which composition comprises an optional new, tannase-producing strain of Lactobacillus plantarum having a pronounced ability to adhere to the human intestinal mucosa.

BACKGROUND

Tannins, defined as water-soluble phenolic products that can precipitate proteins from aqueous solution, are naturally occurring compounds. There are two classes of tannins, the hydrolysable tannins, deriving from gallic acid and ellagic acid, and the condensed tannins, that is proanthocyanidins, which are oligomers and polymers of flavanols. Tannins inhibit the growth of a number of microorganisms and are resistant to microbial attacks (Chung, K. T., et al. (1998), Tannins and human health: A review. Critical Reviews in Food Science and Nutrition 38:421-464. Moulds and yeasts and some aerobic bacteria are usually best fitted to degrade tannins but also anaerobic degradation occurs, e.g. in the intestinal tract (Bhat, T. K., et al. (1998), Microbial degradation of tannins—A current perspective. Biodegradation 9:343-357).

Tannins are known as antinutrients, i.e. they decrease the efficiency of the body to convert digested nutrients to new body substances. However, also health beneficial effects of tannins have been reported, e.g. anticarcinogenic effects, ability to reduce blood pressure and to modulate immune-responses. These effects might be due to the antoxidative properties of tannins (Chung et al. 1998). An efficient antioxidative tannin with reported anticancerogenic properties is ellagic acid. Another type of tannin with exceptional high antioxidative capacity is proanthocyanidins, present in for example grapes and olives. Thus, tannins present in varying concentrations in plant derived foods have profound effects on human health. It is not advisable to ingest large quantities of tannins as they may be involved in cancer formation and anti-nutrition activity, but the intake of small quantity of the correct kind of tannin may be beneficial to human health by affecting the metabolic enzymes, immuno-modulation or other functions (Chung et al. 1998).

However, also the anaerobic breakdown products from many tannins, as produced in the intestinal tract, can generate compounds with health beneficial effects (Bhat et al. 1998). Such breakdown compounds are, for example, derivates of phenylpropionic or phenylacetic acids (Bhat et al. 1998). When absorbed in the GI-tract theses compounds have an anti-inflammatory effect. These compounds together with other breakdown products from tannins have also a wide range antimicrobial effect in the GI-tract, suppressing unwanted bacteria.

PRIOR ART

Most Lactobacillus species are unable to degrade tannins but strains of the closely related species L. plantarum, L. pentosus and L. paraplantarum can posses tannase activity, Osawa, R., et al. (2000), Isolation of tannin-degrading lactobacilli from humans and fermented foods, Applied and Environmental Microbiology 66:3093-3097.

Some Lactobacillus plantarum strains posses a specific ability to adhere to human epithelial cells by a mechanism that is blocked by the presence of mannose, Adlerberth, I., et al., (1996), A mannose-specific adherence mechanism in Lactobacillus plantarum conferring binding to the human colonic cell line HT-29. Applied and Environmental Microbiology 62:2244-2251.

SUMMARY OF THE INVENTION

It has now been found that strains of Lactobacillus plantarum with the ability to adhere to human intestinal mucosa and having the ability to produce tannase, when breaking down tannins, produce compounds that counteract adverse bacteria in the gastrointestinal (GI) tract and have an anti-inflammatory effect when absorbed in the GI-tract.

BRIEF DESCRIPTION OF THE DRAWINGS

The FIGURE shows separated DNA fragments obtained by cleaving chromosomal DNA of the strains Lactobacillus plantarum HEAL 9 (lane 2), HEAL 19 (lane 3), 299v (lane 4) and HEAL 99 (lane 5) with the restriction enzyme EcoRI. High Molecular Weight DNA marker (BRL) and DNA molecular weight marker VI (Roche) were used as standard (lane 1).

DESCRIPTION OF THE INVENTION

The present invention refers to a composition comprising one or more tannase-producing strains of Lactobacillus plantarum or closely related Lactobacillus spp. with ability to adhere to human intestinal mucosa in combination with tannin. Said composition will in vivo produce compounds having an antimicrobial and an anti-inflammatory effect, and in vitro produce compounds having a preservative effect.

The invention also refers to a composition comprising one or more tannase-producing strains of Lactobacillus in combination with tannin and a carrier.

Examples of carriers are oatmeal gruel, lactic acid fermented foods, resistant starch. In order to improve the proliferation of the bacteria and increase the production of anti-inflammatory or preservative derivatives dietary fibres can be added to the composition. Dietary fibres, such as fructo-oligosaccharides, galacto-oligosaccharides, lactulose, malto-dextrins, β-glucans and guar gum, can also be used as a carrier.

The invention especially refers to a food composition comprising a tannase producing strain of Lactobacillus together with more or less pure tannin fractions of, for example, ellagic acid, flavonoids as proanthocyanidins cyanidins and anthocyanidins, or lignans, or with food components rich in tannins, as for example, oats, barley, red sorghum, meal made of the inner cortex of pine tree and juice or extracts from grapes, citrus, lingonberries, blue berries, blackcurrant, cranberries, strawberries, raspberries, and rose hips.

The invention also refers to a pharmaceutical composition comprising a tannase producing strain of Lactobacillus together with more or less pure tannin fractions of, for example, ellagic acid, flavonoids, such as proantho-cyanidins or anthocyanidins, or lignans, or any other pharmaceutically acceptable source of tannin.

In order to achieve a prophylactic or curative effect of the compositions of the invention the content of tannins should preferably be about 500-1000 mg per day. In the case of for instance rose hip powder, this would roughly correspond to 100 g, or in the form of rose hip soup, 4 liter.

Tannins are water-soluble phenolic products of varying molecular weight that can precipitate proteins from aqueous solution. There are two classes of tannins, the hydrolysable tannins, deriving from gallic acid and ellagic acid, and the condensed tannins, that is proanthocyanidins, which are oligomers and polymers of flavanols.

So called condensed, or nonhydrolysable tannins are more resistant to microbial degradation than hydrolysable tannins. Tannins are commonly found in fruit and seeds such as grapes, apple, bananas, blackberries, cranberries, raspberries, strawberries, olives, beans, grains of sorghum, barely and finger millets, coca, tea and coffee.

The composition of the invention can be a food composition wherein the carrier is a food product. In a pharmaceutical composition, the carrier should be a therapeutically acceptable carrier. The composition can be given to the average consumer to improve keep-fit measures in order to prevent eventual future diseases as GI derived infections, diabetes, inflammatory bowel diseases (IBD), irritable bowel syndrome (IBS), cancer or cardio vascular diseases, or to mitigate the exemplified diseases.

The pharmaceutical composition of the invention can be formulated into for instance suspensions, tablets, capsulas, and powders, which can be administrated orally. Said formulations can also be administrated as an enema.

The present invention especially refers to a tannase-producing strain of Lactobacillus plantarum or a closely related Lactobacillus species having the ability to adhere to the human intestinal mucosa, which is characterrised in having a tannase activity determined by the method described by Osawa and Walsh, in Applied and Environmental Microbiology, Vol. 59, No. 4, April 1993, p 1251-1252, disclaiming the strains Lactobacillus plantarum 299, DSM 6595, and Lactobacillus plantarum 299v, DSM 9843.

Preferred tannase producing strains belong to the species Lactobacillus plantarum and have the ability to survive in the gastro-intestinal (GI) tract. Survive in this context means that the strains will have the ability to metabolise and multiply (live) in the GI-tract for a while.

According to a preferred aspect the invention refers to the following new strains, which have all been deposited at the Deutsche Sammlung von Mikroorganismen and Zellkulturen GmbH on Nov. 28, 2002, and been given a deposition number, that is Lactobacillus plantarum HEAL 9, DSM 15312, Lactobacillus plantarum HEAL 19, DSM 15313, and Lactobacillus plantarum HEAL 99, DSM 15316, as well as to variants thereof having essentially the same REA-pattern.

The new strains have been isolated from colonic mucosa of healthy adults and selected by culturing on Rogosa agar. The strains have subsequently been characterised by REA.

According to another aspect the invention also refers to the use of a tannase-producing strain of Lactobacillus plantarum, in combination with tannin for the preparation of a medicament for prophylactic or curative treatment of cardiovascular diseases, inflammatory bowel diseases (IBD), irritable bowel syndrome (IBS), gastrointestinal infections, diabetes, cancer, Alzheimer's disease or diseases with an auto-immune origin. Examples of tannase-producing strains are the new strains HEAL 9, HEAL 19 and HEAL 99, but also the previously known strains Lactobacillus plantarum 299, DSM 6595, and Lactobacillus plantarum 299v, DSM 9843.

The amount of tannase-producing bacteria to be used in the compositions of the invention should preferably not be less than $10^9$ cfu/dose and day.

According to another aspect the invention refers to the use of a tannase-producing strain of Lactobacillus together with tannins for preserving food. Examples of tannase producing strains are the new strains HEAL 9, HEAL 19 and HEAL 99, but also the previously known strains Lactobacillus plantarum 299, DSM 6595, and Lactobacillus plantarum 299v, DSM 9843. Said strains will then produce preservatives directly in the food product out of the degradation of tannins. The tannins could be ensured by either supplementing the product with pure fractions of tannins or by supplementing the product with natural, less defined, supplements rich in tannins, as for example, rose hip, red sorghum or meal made from the inner cortex of pine.

The mixtures of tannin utilizing Lactobacillus strains and tannins can be given for therapeutic purposes or as a keep-fit action in order to decrease risk factors for cardio vascular diseases, the metabolic syndrome, diabetes, inflammatory bowel diseases (IBD), irritable bowel syndrome (IBS), gastro-intestinal infections, or diseases with an auto-immune origin.

The strains L. plantarum HEAL 9, HEAL 19 and HEAL 99 have higher capacity to adhere to human, colonic mucosa cells than the strain Lactobacillus plantarum 299v, DSM 9843.

Experimental

Isolation of Strains 42 different, newly isolated Lactobacillus strains were tested and compared with the well-known probiotic reference strain Lactobacillus plantarum 299v, DSM 9843, for their ability to produce tannase, i.e. to [brake] *break* down tannins. The strains are listed in Table 1 below.

Screening Method

The applied method to detect tannase activity has earlier been described by Osawa and Walsh (1993). The detecting principle is that the breakdown of the tannin, methylgallate, is measured by the following procedure:

The test bacterium is cultured anaerobically on MRSagar (Merck, Darmstadt, Germany) for 2 d at 37° C. and then the cells are harvested and suspended in 5 ml 0.9% (w/v) NaCl. The cell-suspension is centrifuged and the cells re-suspended in 10 ml 0.9% NaCl and the absorbance is measured at 620 nm (0.9% NaCl solution as standard). The cell-suspension is diluted until the absorbance is between 0.1 and 0.6 (spectrophotometer, Pharmacia LKB, Novaspec II). After centrifugation, the cells are re-suspended in 1 ml methylgallate-buffer (3.7 g/l methylgallate [Aldrich Chemical Company, Inc., Milwaukee, Wis., USA], 4.5 g/l $NaH_2PO_4$, pH=5.0 [sterile filtered]) and the tube is incubated at 37° C. for 24 h. One ml of $NaHCO_3$-buffer (42 g $NaHCO_3$ per litre, pH=8.6) is added and the solution is incubated for 1 h at room temperature, before measurement of the absorbance at 440 nm ($NaHCO_3$-buffer as standard). The colour of the suspension is measured by visual determination.

The colour should be brown or green to be graded as positive tannase activity. A quantitative value of the tannase activity was obtained by the ratio between the absorbance of the cell-suspension ($A_{620}$; amount of cells) at the start of the incubation with methylgallate versus the absorbance after the 24 h incubation with methylgallate ($A_{440}$; coloration of free gallic acids after exposure to oxygen in an alkaline condition).

Results

The result of the screening for Lactobacillus strains possessing tannase activity is shown in Table 1. A majority of the tested strains did not have any tannase activity. However, 11 strains were positive and are presented in Table 1.

TABLE 1

Tannase activity in different *Lactobacillus* strains.

| Organism | Strain | Tannase activity* (positive or negative) | Quantitative tannase activity** ($A_{440}/A_{620}$) |
|---|---|---|---|
| *Lactobacillus plantarum* | 299v DSM 9843 | + | 6.2 |
| *Lactobacillus plantarum* | LP2 | + | 4.9 |
| *Lactobacillus plantarum* | LP5 | + | 3.3 |
| *Lactobacillus plantarum* | 4LF:1 | + | 6.1 |
| *Lactobacillus plantarum* | 17LF:1 | + | 5.4 |
| *Lactobacillus plantarum* | HEAL 9 DSM 15312 | + | 6.4 |
| *Lactobacillus plantarum* | HEAL 19 DSM 15313 | + | 7.4 |
| *Lactobacillus plantarum* | HEAL 99 DSM 15316 | + | 6.8 |

*Positive tannase activity is shown as a green to brown coloration of free gallic acid in the cell-suspension after prolonged exposure to oxygen in an alkaline condition.
**The tannase activity expressed as the ratio between the absorbance of the cell-suspension at 620 nm ($A_{620}$) at the start of the 24 h incubation with methylgallate versus the absorbance at 440 nm ($A_{440}$) after the incubation with methylgallate ($A_{440}$).

Three of the tannase positive L. plantarum strains had a higher tannase activity than the well known probiotic strain Lactobacillus plantarum 299v, DSM 9843, i.e. L. plantarum HEAL 9, L. plantarum HEAl 19 and L. plantarum HEAL 99. They have been isolated from healthy, human intestinal mucosa.

Genotypic Identification by REA

The strains were examined as to the cleavage pattern of the chromosomal DNA, through restriction-endonuclease analysis—REA—method according to Ståhl M, Molin G, Persson A, Ahrné S & Ståhl S, International Journal of Systematic Bacteriology, 40:189-193, 1990, and further developed by Johansson, M-L, et al., International Journal of Systematic Bacteriology 45:670-675, 1995. Schematically REA can be described as follows: Chromosomal DNA from the strains involved in the study were prepared and cleaved by restriction endonucleases. 0.75 μg of each DNA was separately digested at 37° C. for 4 h with 10 units of EcoRI and Hind III; each endonuclease was used separately. The cleaved DNA fragments are separated as to size by gel electrophoresis using submerged horizontal agarose slab gels. The gels consisted of 150 ml of 0.9% agarose (ultrapure DNA grade; low electroendo osmosis; BioRad Laboratories, Richmond, USA) and were cast as slab gels (150 by 235 mm). 0.2 μg of the High Molecular Weight DNA marker (Bethesda Research Laboratories, MD, USA) together with 0.5 μg of a DNA molecular weight marker VI (Roche, Germany) were used as standards. Minimal band distortion and maximal sharpness were achieved by applying the sample DNA in Ficoll loading buffer (2 g of Ficoll, 8 ml of water, 0.25% bromphenol).

Gels were run at a constant voltage of 40V for 18 h at about 6-8° C. The buffer (89 mM Tris, 23 mM $H_3PO_4$, 2 mM sodium EDTA, pH 8.3) was recirculated during the running period. Thereafter, the gels were stained for 20 minutes in ethidium bromide (2 μg/ml) and destained in distilled water, visualized at 302 nm with a UV transilluminator (UVP Inc., San Gabriel, USA) and photographed. This way of running the gel electrophoresis gave well distributed and relatively well-separated band down to a molecular weight of $1.2\times10^6$.

The results of the analysis are presented in the FIGURE.

Adhesion to HT-29 Cells

In total 32 L. plantarum strains isolated from human mucosa were tested as to adherence to intestinal epithelial cells of human colonic carcinoma cell-line HT-29 with a mannose-specific binding (method as described by Wold, A, et al, Infection and Immunity, October 1988, p. 2531-2537). Cells of the human adenocarcinoma cell line HT-29 were cultured in Eagle's medium supplemented with 10% fetal calf serum, 2 mM L-glutamine and 50 ig/ml of gentamicin (Sigma Chemical Co., Saint Louis, Mo., USA). A few days after the cells had reached confluence they were detached with EDTA-containing buffer (0.54 mM), washed and suspended in Hank's balanced salt solution (HBSS) at $5\times10^6$/ml. The bacteria were harvested, washed and suspended in HBSS at $5\times10^9$/ml (2× an optical density of 1.5 at 597 nm). Cells, bacteria and HBSS were mixed in the ratio 1:1:3 and incubated with end-over-end rotation for 30 minutes at 4EC. The cells were washed once with ice cold PBS and fixed with neutral buffered formalin (Histofix, Histolab, Götebrog, Sweden). The number of bacteria attached to each of at least 40 cells was determined using interference contrast microscopy (500× magnification, Nicoll Optophot, with interference contrast equipment, Bergström Instruments, Göteborg, Sweden) and the mean number of bacteria per cell was calculated.

All strains except the three HEAL-strains had values between 0.3-14 (adhesion in salt solution; corresponding values in the presence of methyl-mannoside were 0.5 and 2.4, respectively). Most strains had a value lower than 10. The results are given in Table 2 below.

TABLE 2

| Organism | Strain | Adhesion to HT-29 cells (number of bacteria per cell) In salt solution | In presence of methyl-mannoside |
|---|---|---|---|
| *Lactobacillus plantarum* | 299v DSM 9843 | 11.7 | 3.4 |
| *Lactobacillus plantarum* | HEAL 9 | 20 | 2.1 |
| *Lactobacillus plantarum* | HEAL 99 | 20 | 2.0 |
| *Lactobacillus plantarum* | HEAL 19 | 23 | 5.0 |
| *Lactobacillus plantarum* | ATCC 14917$^T$ | 5.2 | 2.2 |
| *Lactobacillus plantarum* | 78B | 0.3 | 0.5 |

Test in Experimental Mouse Model

Method

Fifteen Balb/C mice were divided into five groups (3 mice per group) and fed different combinations of normal food, rose hip powder (rich in tannins) and the tannase positive strain Lactobacillus plantarum 299v. The constituents were mixed with some water to get a mushy consistency. Groups 1 and 2 were given normal mouse food, Group 3 got the normal food supplemented with rose hip powder (1.6 g per day), Group 4 got normal food supplemented with L. plantarum 299v ($10^{10}$ bacteria per dose) and Group 5 got normal food supplemented with both the rose hip powder and L. plantarum 299v. The mice were fed once a day for 6-8 days before inducing an ischemia/reperfusion injury. The injury was done according to the following dissection protocol: Mice were given 0.15 ml of Ketamine/Xylazine solution (7.85 mg/ml and 2.57 mg/ml, respectively) subcutaneously for anesthesia. A midline abdominal incision was made and the superior mesenteric artery was occluded using atraumatic vessel loops and hemostat. 1.0 ml PBS was injected into the peritoneal cavity for fluid resuscitation. The artery was occluded for 30 min before the vessel loop and hemostat were removed and the tissue was observed for immediate reperfusion. The abdomen was then closed using a running vicryl 3-0 suture. The animal was allowed to awake from anesthesia and was removed from the warming pad and placed back into the cage. After 4 h and 15 min, the animal was given anesthesia again and tissue and stool samples were obtained in the following order and placed in preweighed tubes: liver tissue, ilium mesentery tissue and cecum stool for bacteriological sampling, and cecum and ilium tissue for colorimetric assay for lipid peroxidaton, and cecum and ilium tissue for histological examination. The samples for bacteriological evaluation were weighed and placed in freezing media and frozen immediately at −70° C. Samples for colorimetric assay (LPO586) were rinsed in PBS, weighed, homogenized, aliquoted and then frozen immediately at −70° C.

Analysis Methods

Bacteriological evaluation was performed by viable count by anaerobic incubation (BBL Gas Pak Plus, Becton Dickinson and Company, Sparks, Md., USA) on Rogosa-agar (Merck, Darmstadt, Germany) at 37° C. for 3 d, VRBD-agar (Merck, Darmstadt, Germany) at 37° C. for 24 h and Brain heart infusion agar (BHI; Oxoid, Basingstoke, Hampshire, England) at 37° C. for 3 d. Viable count on BHI was also done aerobically.

Colorimetric assay for lipid peroxidation was done with the aid of a spectrophotometer and the analysing kit Bioxytech® LPO-586™ (Oxis Research™, Oxis Health Products, Inc., Portland). The analysis was performed in accordance with the description of the manufacturer.

Lipid peroxidation is a well-established mechanism of cellular injury and is used as an indicator of oxidative stress in cells and tissues. Lipid peroxides are unstable and decompose to form a complex series of compounds including reactive carbonyl compounds. Polyunsaturated fatty acid peroxides generate malondialdehyde (MDA) and 4-hydoxyalkenals (HAE) upon decomposition. Measurement of MDA can be used as indicator of lipid peroxidation. LPO-586™ is a colorimetric assay designed to quantify MDA and is based on the reaction of a chromogenic reagent, N-methyl-2-phenylindole with MDA at 45° C. One molecule of MDA reacts with two molecules of N-methyl-2-phenylindole to yield a stable chromophore with maximal absorbance at 586 nm.

Results

The lipid peroxidation measured as malondialdehyde (MDA) per g colonic tissue was measured in the differently treated mice and the results are presented in Table 3. The ischemia/reperfusion increased the MDA. Pre-treatment of mice with rose hip powder (Group 3) or L. plantarum 299v (Group 4) in the food decreased the MDA compared to the positive control (Group 2). However, the effect of combined pre-treatment with rose hip powder and L. plantarum 299v decreased the MDA much more pronounced (Group 5).

TABLE 3

Lipid peroxidation after ischemia/reperfusion injury in mice.

| Mouse group | Malondialdehyde (MDA) per g colonic tissue [median-value] |
|---|---|
| G1. Control A; uninjured (no ischemia/reperfusion); normal food | 4.3 |
| G2. Control B; normal food | 6.3 |
| G3. Normal food + rose hip powder (RHP) | 5.1 |
| G4. Normal food + *L. plantarum* 299v | 5.8 |
| G5. Normal food + RHP + *L. plantarum* 299v | 3.6 |

The results of the viable count are presented in Table 4. The iscemia/reperfusion injury increased the viable counts on BHI and Rogosa agar with a factor of 10 (compare Group 1 and Group 2). Rose hip powder alone (Group 3) resulted in a lower viable count than the other feeding alternatives. The group that was given both L. plantarum 299v and rose hip powder (Group 5) showed the same viable count as the ischemia/reperfusion injury groups without rose hip powder (Groups 2 and 4) except for Enterobacteriacea that was lower. However, the viable count on the substrate allowing growth of lactobacilli was now (in Group 5) dominated by L. plantarum 299v.

TABLE 4

Bacterial flora in caecum after ischemia/reperfusion injury in mice.

| Mouse | Median of viable count (CFU per g caecal content) | | | |
|---|---|---|---|---|
| | Total anaerobes | Total aerobes | *Lactobacilli* | *Enterobacteriaceae* |
| G1. Control A; uninjured (no ischemia/reperfusion); normal food | $2 \times 10^8$ | $1 \times 10^8$ | $5 \times 10^8$ | $3 \times 10^3$ |
| G2. Control B; normal food | $3 \times 10^9$ | $1 \times 10^9$ | $1 \times 10^9$ | $4 \times 10^3$ |
| G3. Normal food + rose hip powder (RHP) | $1 \times 10^8$ | $4 \times 10^8$ | $1 \times 10^8$ | $<10^2$ |
| G4. Normal food + *L. plantarum* 299v | $3 \times 10^9$ | $4 \times 10^9$ | $2 \times 10^9$ | $3 \times 10^3$ |
| G5. Normal food + RHP + *L. plantarum* 299v | $4 \times 10^9$ | $2 \times 10^9$ | $3 \times 10^9$ | $<10^2$ |

CONCLUSION

The tannins in the rose hip decreased the total load of bacteria in the intestine of the injured mice, but when the mice were administrated L. plantarum 299v simultaneously with rose hip the decrease was mitigated and the tannin-induced reduction was filled up by the L. plantarum 299v. Thus, the tannins supported the balance of the intestinal flora in favour of the probiotic strain. The lipid peroxidation was mitigated by administration of rose hip powder but this effect was enhanced by the presence of L. plantarum 299v together with the rose hip powder.

The strains L. plantarum HEAL 9, HEAL 19 and HEAL 99 have higher tannase activity than L. plantarum 299v and in addition the capacity to adhere to human, colonic mucosa cells are higher than for L. plantarum 299v.

The invention claimed is:

1. A composition comprising:

(a) one or more isolated tannase-producing strains of Lactobacillus plantarum; and (b) tannin;

wherein said one or more isolated tannase-producing strains of Lactobacillus plantarum are selected from the group consisting of: Lactobacillus plantarum strain HEAL 9, which is deposited as DSM 15312; Lactobacillus plantarum strain HEAL 19, which is deposited as DSM 15313; Lactobacillus plantarum strain HEAL 99, which is deposited as DSM 15316; and combinations thereof.

2. The composition according to claim 1, wherein said composition further comprises a carrier.

3. The composition according to claim 1 which is a food composition.

4. The composition according to claim 1 which is a pharmaceutical composition.

5. A isolated tannase-producing strain of Lactobacillus plantarum, wherein said isolated tannase-producing strain of Lactobacillus plantarum is selected from the group consisting of: Lactobacillus plantarum strain HEAL 9, which is deposited as DSM 15312; Lactobacilus plantarum strain HEAL 19, which is deposited as DSM 15313; and Lactobacillus plantarum strain HEAL 99, which is deposited as DSM 15316.

6. The isolated tannase-producing strain according to claim 5, wherein said isolated tannase-producing strain is Lactobacillus plantarum strain HEAL 9, which is deposited as DSM 15312.

7. The isolated tannase-producing strain according to claim 5, wherein said isolated tannase-producing strain is Lactobacillus plantarum strain HEAL 19, which is deposited as DSM 15313.

8. The isolated tannase-producing strain according to claim 5, wherein said isolated tannase-producing strain is Lactobacillus plantarum strain HEAL 99, which is deposited as DSM 15316.

9. A medicament for prophylactic or curative treatment of cardiovascular diseases, diabetes, inflammatory bowel diseases (IBD), irritable bowel syndrome (IBS), gastrointestinal infections, cancer, Alzheimer's disease or diseases with an autoimmune origin, wherein said medicament comprises:

(a) one or more isolated tannase-producing strains of Lactobacillus plantarum having the ability to adhere to the human intestinal mucosa; and (b) tannin;

wherein said one or more isolated tannase-producing strains of Lactobacillus plantarum are selected from the group consisting of: Lactobacillus plantarum strain HEAL 9, which is deposited as DSM 15312; Lactobacillus plantarum strain HEAL 19, which is deposited as DSM 15313; Lactobacillus plantarum strain HEAL 99, which is deposited as DSM 15316; and combinations thereof.

10. A composition for the preservation of food comprising:

(a) one or more isolated tannase-producing strains of Lactobacillus plantarum having the ability to adhere to the human intestinal mucosa; and (b) tannin;

wherein said one or more isolated tannase-producing strains of Lactobacillus plantarum are selected from the group consisting of: Lactobacillus plantarum strain HEAL 9, which is deposited as DSM 15312; Lactobacillus plantarum strain HEAL 19, which is deposited as DSM 15313; Lactobacillus plantarum strain HEAL 99, which is deposited as DSM 15316; and combinations thereof.

11. A food product comprising:

(a) one or more isolated tannase-producing strains of Lactobacillus plantarum having the ability to adhere to the human intestinal mucosa; and (b) tannin;

wherein said one or more isolated tannase-producing strains of Lactobacillus plantarum are selected from the group consisting of: Lactobacillus plantarum strain HEAL 9, which is deposited as DSM 15312; Lactobacillus plantarum strain HEAL 19, which is deposited as DSM 15313; Lactobacillus plantarum strain HEAL 99, which is deposited as DSM 15316; and combinations thereof.

12. The composition according to claim 2 which is a food composition.

13. The composition according to claim 2 which is a pharmaceutical composition.

*14. A method for prophylactic or curative treatment of inflammatory bowel disease (IBD), irritable bowel syndrome (IBS), or gastrointestinal infection comprising administering to an individual with an inflammatory bowel disease (IBD), irritable bowel syndrome (IBS), or a gastrointestinal infection, in combination with a tannin, a tannase-producing strain of Lactobacillus plantarum having the ability to adhere to the human intestinal mucosa, wherein the tannase-producing strain of Lactobacillus plantarum is selected from the group consisting of Lactobacillus plantarum HEAL 9, which is deposited as DSM 15312; Lactobacillus plantarum HEAL 19, which is deposited as DSM 15313; Lactobacillus plantarum HEAL 99, which is deposited as DSM 15316; and combinations thereof.*

* * * * *